United States Patent [19]

Baldwin et al.

[11] Patent Number: 4,665,094
[45] Date of Patent: May 12, 1987

[54] OCULOSELECTIVE BETA-BLOCKERS FOR TREATMENT OF ELEVATED INTRAOCULAR PRESSURE

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 770,479

[22] Filed: Aug. 29, 1985

[51] Int. Cl.$^4$ .................. A61K 31/22; C07C 93/00; C07C 93/06

[52] U.S. Cl. ................... 514/546; 260/501.1; 514/548; 514/554; 514/652; 514/913; 514/555; 548/215; 558/414; 558/422; 560/240; 560/252; 564/349; 564/351

[58] Field of Search ............... 514/554, 555, 652, 546, 514/548, 913; 560/252; 260/465 D, 465 E, 501.1; 564/349, 351

[56] References Cited

U.S. PATENT DOCUMENTS

| | | |
|---|---|---|
| 3,542,872 | 11/1970 | Köppe ................................. 514/652 |
| 3,644,469 | 2/1972 | Koppe et al. ....................... 564/349 |
| 3,663,607 | 5/1972 | Barrett et al. ..................... 560/252 |
| 3,872,147 | 3/1975 | Köppe ................................ 514/652 |
| 3,892,799 | 7/1975 | Pinhas ............................... 514/652 |
| 3,930,016 | 12/1975 | Berntsson et al. ................ 514/652 |
| 4,066,768 | 1/1978 | Raabe et al. ....................... 514/652 |
| 4,171,370 | 10/1979 | Jones et al. ....................... 564/349 |
| 4,450,172 | 5/1984 | Yoo .................................... 514/652 |
| 4,515,814 | 5/1985 | Wick et al. ........................ 564/349 |

FOREIGN PATENT DOCUMENTS

| | | |
|---|---|---|
| 833291 | 3/1976 | Belgium . |
| 0041295 | 12/1981 | European Pat. Off. . |
| 0082461 | 6/1983 | European Pat. Off. . |
| 1966513 | 5/1973 | Fed. Rep. of Germany . |
| 49-11847 | 2/1974 | Japan ................................. 564/349 |
| 1260848 | 1/1972 | United Kingdom . |

Primary Examiner—Vivian Garner
Attorney, Agent, or Firm—William H. Nicholson; Michael C. Sudol; Mario A. Monaco

[57] ABSTRACT

Hydroxyalkyl-phenoxy-propan-2-olamines and novel esters thereof are oculoselective $\beta$-blockers useful in the treatment of elevated intraocular pressure with little or no effect on the pulmonary or cardiovascular system.

6 Claims, No Drawings

OCULOSELECTIVE BETA-BLOCKERS FOR TREATMENT OF ELEVATED INTRAOCULAR PRESSURE

SUMMARY OF THE INVENTION

This invention is concerned with a compound of structural formula I:

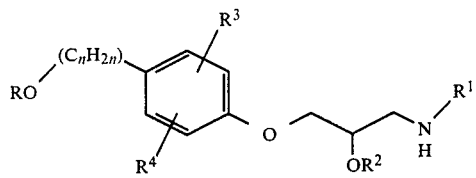

or ophthalmologically acceptable salt thereof, wherein R is hydrogen or alkanoyl, and $R^1$, $R^2$, $R^3$, $R^4$, and n are as herein after defined.

It is also concerned with a method of treating elevated intraocular pressure and the disease states associated therewith, such as glaucoma, by topical ocular administration of a compound of structural formula I wherein R is hydrogen or alkanoyl.

The invention is also concerned with ophthalmic formulations of a compound of structural formula I, and processes for preparing such compounds.

BACKGROUND OF THE INVENTION

Glaucoma is an ocular disorder associated with elevated ocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that a few β-adrenergic blocking agents are effective in reducing intraocular pressure. While many of these agents are effective in reducing intraocular pressure, they also have other characteristics, e.g. local anesthetic activity, that are not acceptable for chronic ocular use.

(S)-1-tert-butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

However, known β-adrenergic blocking agents have not been shown to demonstrate any meaningful oculoselectivity and, in spite of the low dose normally required for ocular administration, manifest their β-blocking properties in extra-ocular tissue, especially the pulmonary and cardiovascular systems to such an extent that they should not be administered to patients with pulmonary or cardiovascular ailments.

Now, with the present invention there are provided compounds, with pronounced oculoselective β-blocking properties with little or no liability by way of extra-ocular β-blocking activity; ophthalmic formulations of those compounds; methods of treating elevated intraocular pressure with those compounds and their ophthalmic formulations and processes for preparation of those compounds.

DETAILED DESCRIPTION OF THE INVENTION

One embodiment of this invention is the novel compound of structural formula Ia:

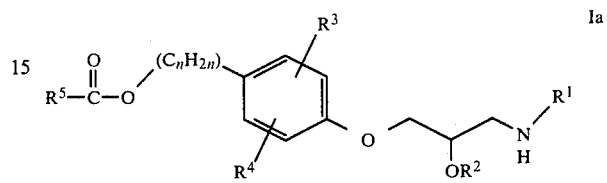

or an ophthalmologically acceptable salt thereof, wherein $R^5$ is $C_{1-5}$alkyl either straight or branched chain;

$R^1$ is $C_{1-5}$alkyl, either straight or branched chain;

$R^2$ is hydrogen or

$R^3$ and $R^4$ are independently
  (1) hydrogen,
  (2) $C_{1-5}$alkyl, either straight or branched chain,
  (3) $C_{1-5}$alkoxy, either straight or branched chain,
  (4) halo, such as fluoro, chloro, bromo or iodo, especially fluoro or chloro, or
  (5) cyano; and n is 1–5, to form a straight or branched chain alkylene.

The ophthalmologically acceptable salts of the compounds of this invention include those prepared from inorganic acids such as hydrochloric, and those formed from organic acids such as maleic acid, citric acid, pamoic acid, pyruvic acid, fumaric acid, oxalic acid, tartaric acid or the like.

All of the novel compounds of this invention are propan-2-olamines or o-alkanoyl derivatives and, of course, the 2-carbon carrying the oxy group is asymmetric. Accordingly the novel compounds have (R)- and (S)-enantiomers.

Also, substituents $R^1$, $R^2$, $R^3$, $R^4$, $R^5$ and —($C_nH_{2n}$)—may themselves be capable of isomerism. This invention includes all of the possible isomers and all of the possible mixtures comprising two or more of those isomers.

For treatment of elevated intraocular pressure it is preferred that n is 2, $R^1$ is t-butyl or isopropyl, $R^2$, $R^3$ and $R^4$ are all hydrogen or one or two of $R^3$ and $R^4$ is lower alkyl, and that $R^5$ is methyl, t-butyl or isopropyl. It is most preferred that n is 2, $R^1$ is t-butyl, $R^2$, $R^3$ and $R^4$ are all hydrogen, and that $R^5$ is methyl, or isopropyl.

A second embodiment of this invention is the novel process for preparing the above described novel compound. It is depicted by the following reaction scheme:

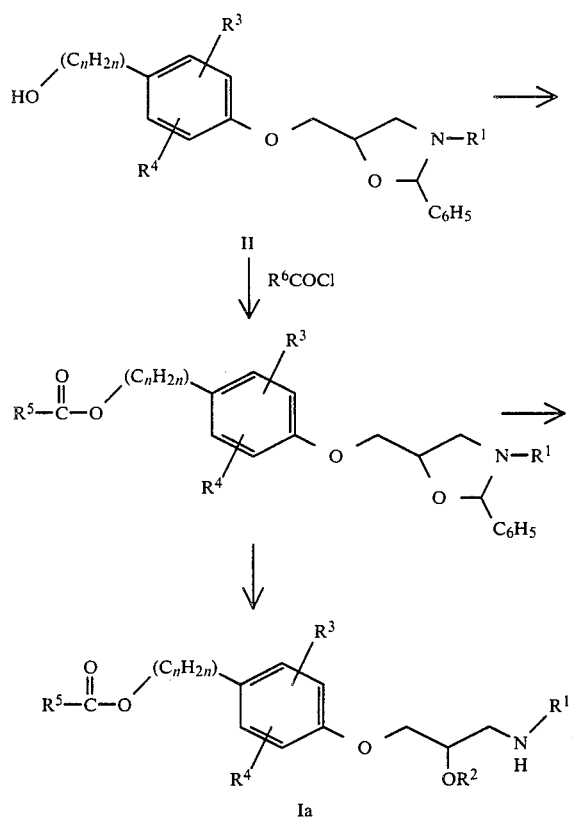

The process comprises treating Compound II with a halide, especially the chloride of structure $R^6COCl$ or an anhydride of structure

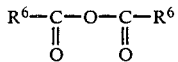

in the presence of at least one equivalent of an acid acceptor such as pyridine, quinoline, or triethylamine in an inert solvent such as dimethylformamide, ethyl acetate, tetrahydrofuran, methylene chloride-ether, benzene or the like. Alternatively, the acid acceptor such as quinoline or pyridine can be used in sufficient excess to act as solvent. The reaction is conducted at about −15° C. to 25° C. for about 1 to 5 hours. Aging for several hours longer at elevated temperatures is not deleterious.

Following isolation of the ester derivative, the oxazolidine ring is opened by treating Compound III with a dilute mineral acid, especially about 0.1 N HCl optionally in the presence of a buffering agent such as sodium acetate, or the like, at about 5° C. to 30° C., preferably room temperature for about 3 to 10 hours.

After isolating the free base, Ia, it may be converted to an acid addition salt, if desired, by dissolving it in an inert organic solvent such as ether, adding a solution of the acid in an inert organic solvent, and collecting the precipitated salt.

The novel esters of formula Ia may also be prepared by esterification of an acid addition salt of the alcohols of formula I (R=H) with one equivalent of an acid halide as described above for acylation of the oxazolidine derivative. Use of an excess of the acid halide permits isolation of the di-alkanoyl compounds, R and $R^2=R^5CO—$.

A third embodiment of this invention is the method of treating elevated intraocular pressure by the topical ocular administration to a patient in need of such treatment of an effective intraocular pressure lowering amount of a compound of formula I:

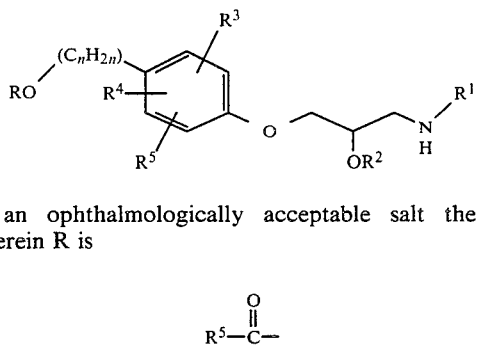

or an ophthalmologically acceptable salt thereof, wherein R is

or H-, and $R^1$, $R^2$, $R^3$, $R^4$, $R^5$, and n are as previously defined.

A unit dose comprises about 0.001 to 5.0 mg, preferably about 0.005 to 2.0 mg, and especially about 0.05 to 1.0 mg of active compound per eye. Multiple unit doses are administered as needed to achieve and maintain a normotensive or close to normotensive ocular condition.

Compounds I (R=H) are generally known compounds (see U.S. Pat. No. 3,872,147 and British Pat. No. 1,260,848). Those that are known, are known primarily as intermediates in the synthesis of the corresponding ethers. They are also known to have weak β-blocking properties on cardiovascular and pulmonary β-receptors, but the outstanding utility of these compounds in preferentially reducing elevated intraocular pressure is not taught nor suggested by any prior art.

A fourth embodiment of this invention is the novel ophthalmic formulations comprising one of the previously mentioned compounds as active ingredient. The ophthalmic composition of this invention may be in the form of a solution, suspension, ointment, gel or solid insert and contain about 0.01 to 5% and especially about 0.5 to 2% by weight of medicament. Higher concentrations as, for example about 10% or lower concentrations can be employed.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600; carbowaxes 1,000, 1,500, 4,000, 6,000 and 10,000; antibacterial components such as quaternary ammonium compounds, phenylmercuric salts known to have cold sterilizing properties and which are non-injurious in use, thimerosal, methyl and propyl paraben, benzyl alcohol, phenyl ethanol; buffering ingredients such as sodium chloride, sodium borate, sodium acetates, gluconate buffers; and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymers.

EXAMPLE 1

(S)-2-(4-(3-((1,1-Dimethylethyl)amino)-2-hydroxypropoxy)phenyl)ethanol maleate

Step A: Preparation of (S)-2-(4-(3-(1,1-dimethylethyl)-2-phenyl-5-oxazolidinylmethoxy)-phenyl)ethanol 4-(2-Hydroxyethyl)phenol (2.5 g, 18 mmol) was dissolved in 37 ml DMF then NaH (60% in mineral oil) (0.72 g, 18 mmol) was added while stirring under $N_2$ atmosphere. After the evolution of $H_2$ ceased, (S)-2-phenyl-5-tosyloxymethyl-3-(1,1-dimethylethyl) oxazolidine (7.0 g, 18 mmol) in 25 ml DMF was added and the reaction mixture was heated at 115°-120° C. for 14 hours. The solvent was evaporated in vacuo. A sodium carbonate solution (100 ml, 20% saturated) was added to the residue and the mixture was extracted with $CHCl_3$ (150 ml then 100 ml). The chloroform was removed in vacuo and the residue was used directly in the next step without further purification.

Step B:
(S)-2-(4-(3-((1,1-Dimethyl)amino)-2hydroxypropoxy)-phenyl)ethanol maleate The residue from Step A was treated with 1N HCl (100 ml) for 4 hours. The aqueous mixture was washed with ether (2×75 ml). The pH was adjusted to 10.5 with 40% NaOH and the mixture was extracted with ether (2×75 ml). The ether extracts were evaporated in vacuo to yield 5.6 g of oil which was dissolved in 100 ml ether. Maleic acid (2.3 g, 19.8 mmol) in 150 ml ether was added dropwise to the ether solution. The white precipitate was isolated by filtration to yield 6 g of product, m.p. 154°-157° C. Approximately 4 g of this material was recrystallized from ethanol-ether to yield 1.8 g of the pure product, m.p.: 161°-162° C.

Anal. Calcd. for $C_{19}H_{29}NO_7$: C, 59.51; H, 7.62; N, 3.65.
Found: C, 59.29; H, 7.89; N, 3.57.

Employing the procedures substantially as described in Example 1, but using the reactants depicted in the following reaction scheme, there are produced the compounds described in Table I:

TABLE I

| Enantiomer | $R^1$ | $R^3$ | $R^4$ | $C_nH_{2n}$ | $[\alpha]_{589}$ | (1)m.p. (°C.) maleate salt |
|---|---|---|---|---|---|---|
| (R)— | —C(CH₃)₃ | H | H | —(CH₂)₂— | +15.8° | 157-159 |

TABLE I-continued

| | | | | | |
|---|---|---|---|---|---|
| (S)— | —CH(CH$_3$)$_2$ | H | H | —C(CH$_3$)$_2$CH$_2$— | |
| (R)— | —CH(CH$_3$)$_2$ | H | H | —C(CH$_3$)$_2$CH$_2$— | |
| (S)— | —C(CH$_3$)$_3$ | 2-CH$_3$ | H | —(CH$_2$)$_2$— | |
| (R)— | —C(CH$_3$)$_3$ | 2-CH$_3$ | H | —(CH$_2$)$_2$— | |
| (S)— | —C(CH$_3$)$_3$ | H | 3-CH$_3$ | —(CH$_2$)$_3$— | |
| (R)— | —C(CH$_3$)$_3$ | H | 3-CH$_3$ | —(CH$_2$)$_3$— | |
| (S)— | —C(CH$_3$)$_3$ | 2-Br | H | —(CH$_2$)$_2$— | |
| (S)— | —C(CH$_3$)$_3$ | 2-Br | 3-CH$_3$ | —(CH$_2$)$_2$— | |
| (S)— | —C(CH$_3$)$_3$ | H | H | —CH$_2$— | 145.5–146 |
| (S)— | —C(CH$_3$)$_3$ | H | H | —CH(CH$_3$)CH$_2$— | |
| (S)— | —C(CH$_3$)$_3$ | H | H | —C(CH$_3$)$_2$CH$_2$— | |
| (S)— | —C(CH$_3$)$_3$ | H | H | —(CH$_2$)$_3$— | 145–147 |
| (S)— | —C(CH$_3$)$_3$ | H | H | —(CH$_2$)$_4$— | |
| (S)— | —C(CH$_3$)$_3$ | H | H | —(CH$_2$)$_5$— | |
| (S)— | —C(CH$_3$)$_3$ | H | H | —CH(CH$_3$)— | 162.5–164 |
| (S)— | —C(CH$_3$)$_3$ | H | H | —C(CH$_3$)$_2$— | |
| (S)— | —C(CH$_3$)$_3$ | 2-Cl | H | —(CH$_2$)$_2$— | |
| (S)— | —C(CH$_3$)$_3$ | 2-Cl | 3-Cl | —(CH$_2$)$_2$— | |
| (S)— | —CH(CH$_3$)$_2$ | 2-CN | H | —(CH$_2$)$_2$— | |
| (S)— | —CH(CH$_3$)$_2$ | 2-O〜H | | —(CH$_2$)$_2$— | |

(1)Optical rotations measured in methanol solution.

EXAMPLE 2

(S)-2-(4-(3-((1,1-Dimethylethyl)amino)-2-hydroxypropoxy)phenyl)ethyl acetate maleate

Step A:

(S)-2-(4-(3-(1,1-dimethylethyl)-2-phenyl-5-oxazolidinylmethoxy)phenyl)ethyl acetate The residue from Example 1, Step A (2.55 g, 6.3 mmol) was dissolved in pyridine (10 ml), cooled to −15° C. and acetyl chloride (547 mg, 6.9 mmol) was added. The mixture was stirred at 0° C. for 3 hours then at room temperature overnight. The solvent was removed in vacuo. To the residue, dil. Na$_2$CO$_3$ solution was added (30 ml) and the mixture was extracted with CHCl$_3$ (50 ml then 20 ml). The combined CHCl$_3$ extracts were washed with H$_2$O (30 ml), dried over Na$_2$SO$_4$ and evaporated in vacuo. The residue was used directly in the next step without further purification.

Step B:

(S)-2-(4-(3-((1,1-Dimethylethyl)amino)-2-hydroxypropoxy)phenyl)ethyl acetate maleate To the residue from step A, sodium acetate (4.1 g, 0.05 mol) and 1NHCl (50 ml) were added and the mixture was stirred at room temperature for 7 hours. The aqueous mixture was washed with ether (2×30 ml), made basic (pH 10) with 10N NaOH and extracted with CHCl$_3$. The solvent was removed in vacuo and the product was purified on silica gel using CHCl$_3$—CH$_3$OH—H$_2$O systems of increasing polarity as the eluent to yield 460 mg of product. This product (460 mg, 1.48 mmol) was dissolved in 5 ml ether and maleic acid (172.5 mg, 1.48 mmol) in 15 ml ether was added. The crystals were separated by filtration and dried in vacuo to yield 410 mg (15.2%) of product. m.p. 143°–5° C.

Anal. Calcd. for C$_{17}$H$_{27}$NO$_4$C$_4$H$_4$O$_4$: C, 59.28; H, 7.34; N, 3.29.

Found: C, 59.33; H, 7.59; N, 3.49.

Employing the procedures substantially as described in Example 2, using the reactants depicted in the following reaction scheme, there are produced the novel compounds described in Table II:

TABLE II

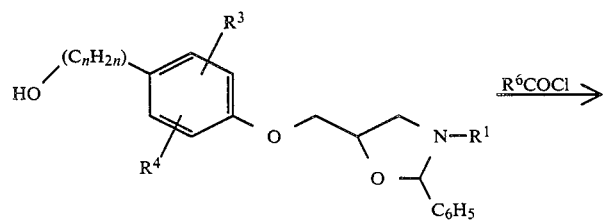

TABLE II-continued $$R^5\overset{O}{\underset{\|}{C}}-O-(C_nH_{2n})-\text{Ar}(R^3,R^4)-O-CH_2-CH(O-CH(C_6H_5))-CH_2-N-R^1 \xrightarrow{H^+}$$

$$R^5-\overset{O}{\underset{\|}{C}}-O-(C_nH_{2n})-\text{Ar}(R^3,R^4)-O-CH_2-CH(OR^2)-CH_2-\overset{R^1}{\underset{H}{N}}$$

| Enantiomer | $R^5$—CO— | $R^1$ | $R^3$ | $R^4$ | $C_nH_{2n}$ | $[\alpha]_{589}$ (CH$_3$OH) | m.p. (°C.) maleate salt |
|---|---|---|---|---|---|---|---|
| (S)— | (CH$_3$)$_3$CCO— | —C(CH$_3$)$_3$ | H | H | —(CH$_2$)$_2$— | | 169–170 |
| (R)— | CH$_3$CO— | —C(CH$_3$)$_3$ | H | H | —(CH$_2$)$_2$— | +14.6° | 142–145 |
| (S)— | (CH$_3$)$_2$CHCO— | —C(CH$_3$)$_3$ | H | H | —(CH$_2$)$_2$— | −13.5° | 151–153 |
| (S)— | CH$_3$CO— | —CH(CH$_3$)$_2$ | H | H | —C(CH$_3$)$_2$CH$_2$— | | |
| (R)— | CH$_3$CO— | —CH(CH$_3$)$_2$ | H | H | —C(CH$_3$)$_2$CH$_2$— | | |
| (S)— | CH$_3$CO— | —C(CH$_3$)$_3$ | 2-CH$_3$ | H | —(CH$_2$)$_2$ | | |
| (R)— | CH$_3$CO— | —C(CH$_3$)$_3$ | 2-CH$_3$ | H | —(CH$_2$)$_2$ | | |
| (S)— | CH$_3$CO— | —C(CH$_3$)$_3$ | H | 3-CH$_3$ | —(CH$_2$)$_3$— | | |
| (R)— | CH$_3$CO— | —C(CH$_3$)$_3$ | H | 3-CH$_3$ | —(CH$_2$)$_3$— | | |
| (S)— | CH$_3$(CH$_2$)$_3$CO— | —C(CH$_3$)$_3$ | 2-Br | H | —(CH$_2$)$_2$— | | |
| (S)— | (CH$_3$)$_2$CHCH$_2$CO— | —C(CH$_3$)$_3$ | 2-Br | 3-CH$_3$ | —(CH$_2$)$_2$— | | |
| (S)— | CH$_3$CH$_2$CHCO—<br>    \|<br>   CH$_3$ | —C(CH$_3$)$_3$ | H | H | —CH$_2$— | | 145.5–146 |
| (S)— | (CH$_3$)$_3$CCO— | —C(CH$_3$)$_3$ | H | H | —CH(CH$_3$)CH$_2$— | | |
| (R)— | CH$_3$CO— | —C(CH$_3$)$_3$ | H | H | —C(CH$_3$)$_2$CH$_2$— | | |
| (S)— | (CH$_3$)$_2$CHCO— | —C(CH$_3$)$_3$ | H | H | —(CH$_2$)$_3$— | | 145–147 |
| (S)— | CH$_3$CO— | —C(CH$_3$)$_3$ | H | H | —(CH$_2$)$_4$— | | |
| (R)— | CH$_3$CO— | —C(CH$_3$)$_3$ | H | H | —(CH$_2$)$_5$— | | |
| (S)— | CH$_3$CO— | —C(CH$_3$)$_3$ | H | H | —CH(CH$_3$)— | | 162.5–164 |
| (R)— | CH$_3$CO— | —C(CH$_3$)$_3$ | H | H | —C(CH$_3$)$_2$— | | |
| (S)— | CH$_3$CO— | —C(CH$_3$)$_3$ | 2-Cl | H | —(CH$_2$)$_2$— | | |
| (R)— | CH$_3$CO— | —C(CH$_3$)$_3$ | 2-Cl | 3-Cl | —(CH$_2$)$_2$— | | |
| (S)— | CH$_3$CO— | —CH(CH$_3$)$_2$ | 2-CN | H | —(CH$_2$)$_2$— | | |
| (S)— | CH$_3$CO— | —CH(CH$_3$)$_2$ | 2-O~~ | H | —(CH$_2$)$_2$— | | |

EXAMPLE 3

(S)-2-(4-(3-((1,1-Dimethylethyl)amino)-2-acetoxypropoxy)phenyl)ethyl acetate maleate To a solution of (S)-2-(4-(3-(1,1-dimethylethyl)amino)-2-hydroxypropoxy)phenyl ethanol (10.2 g, 0.038 mol) in absolute ethanol was added a 4.65N solution of HCl in ethanol (10 ml, 0.046 mol). The mixture was concentrated to dryness and the residue flushed with toluene to give the hydrochloride salt (11.6 g, 0.038 mol). To a suspension of the salt in methylene chloride (200 ml), cooled to 0° C. was added dropwise a solution of acetyl chloride (2.7 ml, 0.038 mol) in methylene chloride (50 ml). The reaction was stirred at room temperature for 75 minutes, additional acetyl chloride (0.2 ml, 0.002 mol) added and the reaction continued at room temperature overnight. Another 0.05 equivalent of acetyl chloride was then added and the reaction stirred for 1 hour. The solution was washed with saturated NaHCO$_3$ solution, water, brine, dried and concentrated to dryness to yield an oil (9.6 g); column chromatography (silica gel, 100% CHCl$_3$ saturated with ammonia) permitted the isolation of two products, the primary alcohol acetate described in Example 2 (7.8 g) and the free base of the desired diacetate (1.6 g). Addition of maleic acid (0.5 g, 0.004 mol) to a solution of the diacetate in acetonitrile afforded the product salt (1.2 g); m.p. 154°–156° C.

Compounds described herein have been studied with respect to their ability, on topical administration, to lower intraocular pressure of rabbits with experimental glaucoma induced by intraocular injection of α-chymotrypsin. These studies demonstrate that the compounds, in general, are effective in lowering intraocular pressure after topical application.

Examples of topical ocular formulations follows:

EXAMPLE 4

| Solution Composition | |
| --- | --- |
| (S)—2-(4-(3-((1,1-Dimethyl-ethyl)amino)-2-hydroxy-propoxy)phenyl)ethyl acetate maleate | 6.8 mg. |
| Sodium Chloride | 7.4 mg. |
| Benzalkonium chloride | 0.10 mg. |
| Sodium acetate anhydrous | 0.82 mg. |
| Water for injection q.s. ad. | 1.0 ml. |

The active compound, salts, and benzalkonium chloride are added to and dissolved in water and the final solution diluted to volume. The solution is rendered sterile by filtration through a sterilizing filter.

EXAMPLE 5

| (S)—2-(4-(3-((1,1-Dimethyl-ethyl)amino)-2-hydroxy-propoxy)phenyl)ethyl acetate maleate | 5 mg. |
| --- | --- |
| Petrolatum q.s. ad. | 1 gram |

The active compound and the petrolatum are aseptically combined.

EXAMPLE 6

| (S)—2-(4-(3-((1,1-Dimethyl-ethyl)amino)-2-hydroxy-propoxy)phenyl)ethyl acetate maleate | 1 mg. |
| --- | --- |
| Hydroxypropylcellulose q.s. | 12 mg. |

Ophthalmic inserts are manufactured from compression molded films which are prepared on a Carver Press by subjecting the powder mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for ½ hour.

EXAMPLE 7

| (S)—2-(4-(3-((1,1-Dimethyl-Methyl)amino)-2-hydroxy-propoxy)phenyl)ethyl acetate maleate | 1 mg. |
| --- | --- |
| Hydroxypropyl cellulose q.s. ad. | 12 mg. |

Ophthalmic inserts are manufactured from a solvent cast film prepared by making a viscous solution of the powder using methanol as the solvent. The solution is placed on a Teflon plate and allowed to dry at ambient conditions. After drying, the film is placed in an 88% R.H. cabinet until it is pliable. Appropriately sized inserts are cut from the film.

EXAMPLE 8

| (S)—2-(4-(3-((1,1-Dimethyl-ethyl)amino)-2-hydroxy-propoxy)phenyl)ethyl acetate maleate | 1 mg. |
| --- | --- |
| Hydroxypropyl methyl cellulose q.s. ad. | 12 mg. |

Ophthalmic inserts are manufactured from a solvent case film which is prepared by making a viscous solution of the powder blend using a methanol/water solvent system (10 ml. methanol is added to 2.5 g. of powder blend, to which 11 ml. of water (in three divided portions) is added. The solution is placed on a Teflon plate and allowed to dry at ambient conditions. After drying, the film is placed in an 88% R.H. cabinet until it is pliable. Appropriately sized inserts are then cut from the film.

EXAMPLE 9

| (S)—2-(4-(3-((1,1-Dimethyl-ethyl)amino)-2-hydroxy-propoxy)phenyl)ethyl acetate maleate | 1 mg. |
| --- | --- |
| Hydroxypropymethyl cellulose q.s. ad. | 12 mg. |

Ophthalmic inserts are manufactured from compression molded films which are prepared on a Carver Press by subjecting the powder mixture of the above ingredients to a compressional force of 12,000 lbs. (guage) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for one-half hour.

What is claimed is:

1. The compound (R)- or (S)-2-(4-(3-((1,1-dimethylethyl)amino)-2-hydroxypropoxy) phenyl)-ethyl acetate, [2-(4-(3-((1,1-dimethylethyl)amino) 2-hydroxypropoxy)phenyl)ethyl 2,2-dimethylacetate] or an ophthalmologically acceptable salt thereof.

2. The (S)-enantiomer of claim 1 or an ophthalmologically acceptable salt thereof.

3. A method of treating elevated intraocular pressure in a patient in need of such treatment which comprises the topical ocular administration of an effective intraocular pressure lowering amount of the compound (R)- or (S)-2-(4-(3-((1, 1-dimethylethyl)amino)-2-hydroxypropoxy)phenyl)ethyl acetate, [2-(4-(3-((1,1-dimethylethyl)amino)-2-hydroxypropoxy) phenyl)ethyl 2,2-dimethylacetate] or an ophthalmologically acceptable salt thereof.

4. The method of claim 3, wherein the compound is the (S)-enantiomer.

5. An ophthalmic formulation for the topical ocular treatment of elevated intraocular pressure comprising an ophthalmologically acceptable carrier and an effective amount of the compound (R)- or (S)-2-(4-(3-((1,1- dimethylethyl)amino)-2-hydroxypropoxy) phenyl)ethyl acetate[; 2-(4-(3-((1,1-dimethylaethyl)amino)2-hydroxypropoxy) phenyl)ethyl 2,2-dimethylacetate] or an ophthalmologically acceptable salt thereof.

6. The formulationo of claim 2 wherein the compound is the (S)-enantiomer of 2-(4-(3-((1,1-dimethylethyl) amino)-2-hydroxypropoxy)phenyl)ethyl acetate[; [2-(4-(3-((1,1-dimethylethyl)amino)-2-hydroxypropoxy)phenyl) ethyl acetate 2,2-dimethylacetate] or an ophthalmologically acceptable salt thereof.

* * * * *